United States Patent [19]

Wrasidlo

[11] Patent Number: 5,155,210
[45] Date of Patent: Oct. 13, 1992

[54] METHODS OF CONJUGATING ACTINOMYCIN D

[75] Inventor: Wolfgang A. Wrasidlo, La Jolla, Calif.

[73] Assignee: Brunswick Corporation, Skokie, Ill.

[21] Appl. No.: 580,835

[22] Filed: Sep. 11, 1990

[51] Int. Cl.$^5$ .................. C07K 5/12; C07K 17/02; A61K 39/44
[52] U.S. Cl. .................. 530/317; 530/323; 530/345; 530/391.7; 530/391.9; 530/399; 530/404; 530/405; 530/408; 530/409; 424/85.91
[58] Field of Search ............ 530/317, 323, 345, 405, 530/404, 408, 409, 388, 390, 391, 399, 391.7, 391.9; 424/85.91

[56] References Cited

U.S. PATENT DOCUMENTS

| | | | |
|---|---|---|---|
| 4,385,169 | 5/1983 | Kato et al. | 528/321 |
| 4,507,234 | 3/1985 | Kato et al. | 530/363 |
| 4,543,211 | 9/1985 | Kato et al. | 530/391.9 |
| 4,562,176 | 12/1985 | Sengupta | 514/17 |
| 4,671,958 | 6/1987 | Rodwell et al. | 424/85.91 |
| 4,680,382 | 7/1987 | Sengupta | 530/317 |
| 4,861,581 | 8/1989 | Epstein et al. | 424/1.1 |
| 4,882,423 | 11/1989 | Taguchi et al. | 530/380 |
| 4,952,394 | 8/1990 | Senter | 424/85.91 |
| 4,966,577 | 10/1990 | Crosson et al. | 604/20 |
| 5,019,368 | 5/1991 | Epstein et al. | 424/1.1 |

OTHER PUBLICATIONS

Creech (1952) Cancer Res. 12:557–564.
Erlanger (1980) Methods Enzymol 70:85–104.
Fujiwara et al (1988) Cancer Res. 48:4843–4847.
Blair et al (1983) J. Immunol Methods 59:129–143.
Teijin and Yoshinori, "Cytocidal Modified Immunoglobulin and it Preparation," Patent Abstracts of Japan vol. 9:39 C 291, (1985), Patent No. 60-41617.
Hashimoto et al., "An approach to cancer chemotherapy by application of monoclonal antibody-modified liposomes," Chemical Abstracts vol. 104:394 (1986), Abstract No. 116021c.
Hashimoto et al., "Antitumor effect of antinomycin D entrapped in liposomes bearing subunits of tumor-specific monoclonal immunoglobulin M antibody," Chemical Abstracts vol. 100:355 (1084), Abstract No. 126820u.

*Primary Examiner*—Christine M. Nucker
*Assistant Examiner*—Kay K. Kim
*Attorney, Agent, or Firm*—Campbell and Flores

[57] ABSTRACT

The invention provides for antinomycin D derivatives and methods of producing antinomycin D derivatives. Such derivatives include isocyanate, thioisocyanate, carboxylic acid, bromide, aldehyde and sulfonic acid derivatives. The invention also provides for actinomycin D derivatives conjugated to target cell binding proteins. Methods are provided to make such conjugates through attachment of the derivatized moiety to a reactive group on a target cell binding protein or on a spacer. The conjugates can be administered to an animal and produce localized cytotoxic effects on target cells.

6 Claims, 2 Drawing Sheets

METHODS OF CONJUGATING ACTINOMYCIN D

BACKGROUND OF THE INVENTION

This invention relates to conjugates of antibodies and therapeutic agents and, more specifically, to therapeutic preparations of actinomycin D linked to an antibody for delivery of actinomycin D to the site of action as dictated by the antibody specificity.

It has long been recognized as highly desirable to specifically target therapeutic agents to invading organisms or diseased cells. Specific targeting permits lower doses of the therapeutic agent to be given and reduces the observed side effects from non-specific action of the agent. Various target cell binding agents, such as liposomes, proteins and antibodies, have been used in conjunction with pharmaceutical or cytotoxic agents, such as microbial toxins, protein synthesis inhibitors (i.e. diphtheria toxin) and radioactive compounds as specific targeting molecules.

Antibodies, particularly monoclonal antibodies, which recognize specifically selected antigens are especially suited for delivery of therapeutic agents. Monoclonal antibodies are advantageous since they have the ability to recognize a single molecular site or epitope on a cell. Studies have identified monoclonal antibodies specifically directed toward tumor-associated antigens and other antigens on cancer cells, T-cells and B-cells. These monoclonal antibodies can be used to deliver drugs directly and specifically to the target cells. One of the potential means of attacking such target cells is to use the monoclonal antibodies with an attached drug, such as an antibiotic. Delivery of antibody-therapeutic agent to specific cells, tissues, organs, or any other site in vivo can be accomplished using whole antibodies or fragments of antibodies. Fragments, such as Fab, can be used in place of whole antibodies if they retain the ability to recognize selected antigens.

Conjugates of antibody-therapeutic agent can be made by chemically coupling the two through covalent bonds. One disadvantage of covalent attachment to the backbone of an antibody molecule is that if the chemical modification is in the antigen binding region, the recognition of the antibody can be changed. This adverse effect on the functional properties of the antibody has been a problem with the random linkage of drugs to antibodies. The critical features of the resulting conjugate are that it maintain its biological activity, (both the antibody and therapeutic agent) and that it be stable for use in vivo. The attachment of the therapeutic agent to the target cell binding protein must be stable in all conditions of administration to a patient and under all conditions present in the microenvironment at the site of action. Further, for administration of an effective amount in a human or animal, the conjugate must remain immunospecific for an antigenic determinant on specific cells or tissues.

Actinomycin D is an antibiotic which inhibits RNA transcription, the process by which genetic information in one strand of DNA is copied into a complementary set of bases called messenger RNA (mRNA). Actinomycin D intercalates, or inserts itself, into the double-helical DNA between G≡C base pairs causing a deformed DNA template, thereby preventing efficient RNA transcription. In essence, actinomycin D jams the DNA zipper.

Further, actinomycin D is especially attractive due to its effectiveness at low concentrations. In low concentrations, actinomycin D inhibits transcription without appreciably affecting DNA replication or protein synthesis. It has been extensively used as a highly specific inhibitor of the formation of new RNA in both procaryotic and eucaryotic cells which eventually results in the death of the cells. Additionally, its inhibition of the growth of rapidly dividing cells makes it an effective non-selective therapeutic agent in the treatment of some cancers.

The chemistry for attaching actinomycin D to selective targeting agents has been burdened with unwanted side products and all attempts have been unsuccessful.

There thus exists a need for target cell binding agents conjugated to actinomycin D which can be used for therapeutic or diagnostic purposes. Preferably, such a conjugate should be stable in vivo. The present invention satisfies these needs and provides related advantages as well.

SUMMARY OF THE INVENTION

The invention provides actinomycin D derivatives and methods of producing actinomycin D derivatives, which are useful for conjugating actinomycin D to other materials. Such derivatives include isocyanate, thioisocyanate, carboxylic acid, bromine, aldehyde and sulfonic acid derivatives. The invention also provides for actinomycin D derivatives conjugated to target cell binding proteins. Methods are provided for synthesizing such conjugates through attachment of the derivative to a reactive group on a target cell binding protein or a spacer. The conjugates can be administered to an animal and produce localized cytotoxic effects on target cells.

DETAILED DESCRIPTION OF THE INVENTION

Figure 1A:
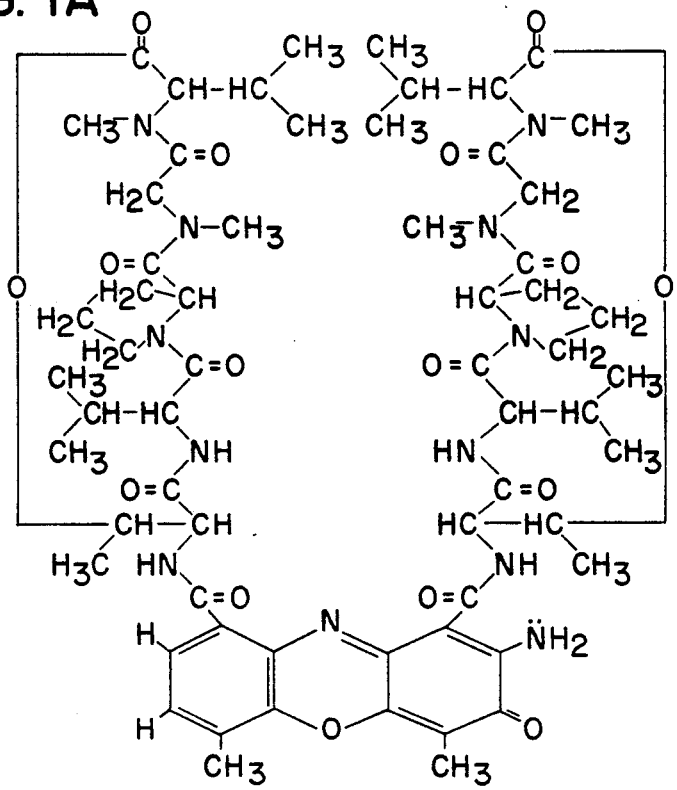
FIG. 1a shows the structure of actinomycin D.
Figure 1B:
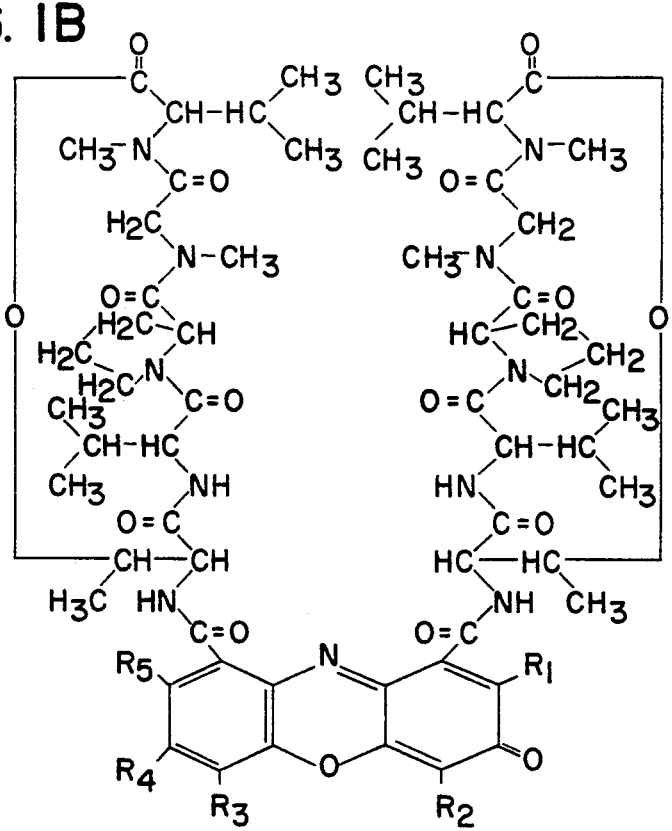
FIG. 1b shows locations of the moieties, represented as $R_1$ through $R_5$, on the aromatic component of actinomycin D which can be modified.

This invention is directed to simple and efficient methods for producing chemical derivatives of actinomycin D and methods for coupling such derivatives to target cell binding proteins to produce actinomycin D conjugates. Until now, such actinomycin D conjugates did not exist because the chemistry for producing actinomycin D derivatives was burdened with unwanted side products. An important advantage of producing chemical derivatives of actinomycin D and actinomycin D conjugates is that the actinomycin D antibiotic is a very potent inhibitor of RNA synthesis in virtually all types of cells. Coupling the actinomycin D derivative to a target cell binding protein allows the specific killing of any cell type to which a target cell binding protein is available. Thus, the actinomycin D conjugates produced from the chemical derivatives of actinomycin D are applicable in specifically suppressing tumor growth in patients and in suppressing contaminating cell growth in culture.

In one embodiment, the method for producing chemical derivatives of actinomycin D involves the formation of an isocyanate derivative of actinomycin D. Actinomycin D has a single primary amine located on the three-ring aromatic component of the molecule. Reacting oxalyl chloride with actinomycin D converts the primary amine into an isocyanate moiety. The isocyanate moiety is reactive with chemical groups on the target cell binding protein such as the hydroxyl moieties of serine and the primary amine moieties of lysine. Coupling of the isocyanate moiety to hydroxyl or primary amine groups on target cell binding proteins produces an actinomycin D conjugate useful for selectively suppressing target cell growth.

Alternatively, the isocyanate derivative of actinomycin D can be coupled to a target cell binding protein through a spacer. The spacer can be attached at one end to the isocyanate moiety through a hydroxyl or primary amine reactive group. The other end of the spacer will have a chemical moiety, such as a carboxylic acid, capable of being coupled to a target cell binding protein.

In other embodiments of the invention, methods for producing a variety of other actinomycin D derivatives are provided. These methods involve the modification of the primary amine of actinomycin D to produce other isocyanate derivatives as well as thioisocyanate and carboxylic acid derivatives. Methods involving the modification of the aromatic methyl group substituents to produce methylene bromide and aldehyde derivatives of actinomycin D are also provided. Additionally, sulfonic acid derivatives of actinomycin D can be produced by replacing the aromatic hydrogen atoms. Each of the above derivatives can be coupled to a target cell binding protein through the derivatized moiety to produce actinomycin D conjugates for use in specifically suppressing target cell growth.

As used herein, the term "target cell binding protein" refers to a protein which exhibits selective binding to a target cell. The protein can be, for example, a monoclonal antibody, polyclonal serum, protein hormone, growth factor and cell surface binding protein such as a cell adhesion protein. The term is also meant to include functional fragments of target cell binding proteins. "Functional fragments," as used herein, refers to fragments which exhibit the selective binding properties to a target cell of the intact molecule. Selective binding indicates binding specificity and affinity of the target cell binding protein for the target cell. The molecule being bound on the target cell is typically a cell surface molecule, such as a protein antigen, although carbohydrate, lipid, inorganic molecules such as phosphate and sulphate, polypeptide and peptide molecules can also be bound as well so long as the target cell binding protein exhibits selective binding for these molecules. The target cell can be any cell or population of cells which contains a cell surface molecule capable of being bound by the target cell binding protein. Cells in culture are included as well as cells within an organism.

As used herein, the term "actinomycin D derivative" refers to a modified form of actinomycin D. Actinomycin D is the compound shown in FIG. 1*a*. There are five moieties on actinomycin D which can be modified. The moieties are located on the three-ring aromatic component of actinomycin D and are replaced in FIG. 1*b* as groups $R_1$ through $R_5$. Reference to these moieties in chemical equations will be diagrammed as the moiety attached to the letters "AMD", where AMD represents the rest of the actinomycin D molecule. For example, $R_1$, which is the primary amine on the aromatic component of actinomycin D, will be represented as AMD—$NH_2$. Modifications of such moieties to produce an actinomycin D derivative can include, for example, addition of chemical groups or substitution. Actinomycin D derivatives include, for example, isocyanate derivatives, carboxylic acid derivatives, methylene bromide derivatives, thioisocyanate derivatives, aldehyde derivatives, and sulfonic acid derivatives. Such derivatives will also be represented in the same manner as that described above.

As used herein, the term "actinomycin D conjugate" or "conjugate" refers to an actinomycin D derivative coupled to a target cell binding protein. The term "coupled," as used herein, refers to the joining of two molecules together, such as through a covalent bond between an actinomycin D derivative and a target cell binding protein. The two molecules can also be an actinomycin D derivative and a spacer. Therefore, the coupling of an actinomycin D derivative can be through direct coupling to the target cell binding protein or coupling through a spacer molecule.

As used herein, the term "reactive group" refers to a chemical moiety which exhibits bond formation activity. Coupling a molecule through a reactive group results in bond formation between the molecule and the reactive group. Reactive groups can be, for example, primary amines, hydroxyls, carboxylic acids, isocyanates, aldehydes, sulfonic acids, and methylene bromides. Bond formation includes prior activation of the chemical moiety to achieve bond formation.

The term "activation," as used herein, refers to a chemical reaction which results in modification of the chemical reactivity of a chemical moiety. The modification typically does not change greatly the chemical specificity of the moiety, but instead, allows the moiety to be reacted faster, more easily and often with the production of fewer side products. Activation of carboxylic acid moiety with, for example, carbodiimide, N-hydroxysuccinimide, N-ethoxycarbonyl-2-ethoxy-1,2-dihydroquinoline (EEDQ) or isobutyl chloroformate, allows rapid and efficient coupling of the activated carboxylic acid moiety to a primary amine to form an amide bond. Other activating reagents include, for example, isocyanates, thioisocyanates, azides and diazo-halides. The preferred activating reagent will depend on the particular chemical moiety involved and on the desired bond to be produced. Such reactions are known to one skilled in the art.

As used herein, the term "spacer" refers to a molecule which forms a bridge-like structure between an actinomycin D derivative and a target cell binding protein. The spacer can be used, for example, as an alternative means for coupling an actinomycin D derivative to a target cell binding protein other than directly through reactive groups on the two molecules. Such spacers can consist of one or more atoms but are preferably less than about twenty atoms in length. Spacers can be bifunctional, or more preferably, heterobifunctional; both types of spacers contain reactive groups on each end of the molecule useful in coupling actinomycin D derivatives to an antibody. Bifunctional spacers have the same reactive group on each end. Heterobifunctional spacers, on the other hand, have different reactive groups at each end. Heterobifunctionality is beneficial because it reduces crosslinking and the production of unwanted side products in the coupling reaction. Heterobifunctional spacers include, for example, hydrocarbons of less than about twenty carbon atoms in length, preferably about ten, with one of a variety of chemical moieties at one end and a different chemical moiety at the other end. Preferably, a carboxylic acid group is included as one of the chemical moieties. The other end can contain one of a variety of chemical moieties which will depend on the chemistry necessary for coupling to an actinomycin D derivative.

Peptide spacers are also included which have, for example, the structure: R—Peptide—$R_1$—COOH. R corresponds to the actinomycin D reactive end and includes such chemical moieties as oximes ($H_2N$—O), phenylhydrazines ($H_2N$—NH—Ph), hydrazides ($H_2N$—NH—CO), and hydrazine-sulfonyl ($H_2N$—NH—$SO_2$—Ph). Other chemical moieties are also included such as hydroxyl, primary amine, aromatic oxygens and brominated methylene groups. $R_1$ corresponds to the target cell binding protein reactive end and can include, for example, structures such as maleic acid, succinic acid, citraconic acid, diglyconic acid, and dimethylmaleic acid. The peptide can be of any length and sequence but is preferably about three to four amino acids in length. The sequence is preferably Ala-Ala-Ala, Ala-Leu-Ala-Leu, Leu-Ala-Leu-Ala or Ser-Ser-Ser.

The invention provides an isocyanate derivative of actinomycin D as well as a method for producing such isocyanate derivatives of actinomycin D. Actinomycin D contains a single primary amine which can be converted to an isocyanate moiety by reaction with a compound such as oxalyl chloride. The reaction with oxalyl chloride is as follows:

where AMD—$NH_2$ represents the primary amine of actinomycin D.

Compounds similar to oxalyl chloride can also be used to produce other isocyanate derivatives of actinomycin D as well as carboxylic acid and thioisocyanate derivatives. Such compounds include, for example, acid chlorides of the structure Cl—CO—R—X where R is a hydrocarbon and X can be an isocyanate, carboxylic acid or thioisocyanate. Reaction of this acid chloride with the primary amine of actinomycin D produces an amide bond between the primary amine and the carbonyl group of the acid chloride. The resultant derivative has the structure AMD—NH—CO—R—X. Other chemical moieties can be used as well, such as an aldehyde group, in place of the acid chloride moiety of the above structure. Therefore, the invention provides for a variety of isocyanate, carboxylic acid and thioisocyanate derivatives as well as methods of producing such derivatives.

The invention also provides for a carboxylic acid derivative of actinomycin D with a structure different than that described above and a method of producing such carboxylic acid derivatives as well. Reaction of actinomycin D with brominated carboxylic acids, such as bromoacetic acid, releases hydrogen bromide and forms a bond between the primary amine located on actinomycin D and the methylene group of bromoacetic acid. The reaction is depicted as follows and results in secondary amine formation:

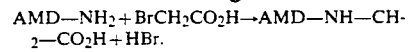

Halogen atoms other than bromine can also be used in the carboxylic acid reactant. Such halogen atoms can be, for example, chloro or iodo and are known to those skilled in the art.

The invention further provides for a methylene bromide derivative of actinomycin D as well as a method of producing such a derivative. Reaction of bromine or bromotrichloromethane, for example, with actinomycin D in the presence of ultraviolet light brominates the methyl group substituents of the aromatic rings. Alternatively, bromination, such as that shown below, will also result in a methylene bromide derivative of actinomycin D.

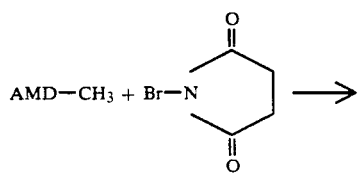

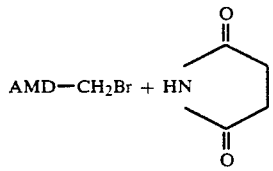

where AMD—$CH_3$ represents either of the two aromatic methyl group substituents on actinomycin D.

The invention further provides for aldehyde derivatives of actinomycin D and methods for producing such derivatives. The aromatic methyl group substituents of actinomycin D can be selectively oxidized as follows to produce an aldehyde derivative:

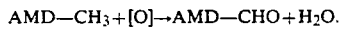

The invention also provides for sulfonic acid derivatives and a method of producing sulfonic acid derivatives. The two aromatic hydrogen atoms of actinomycin D can be reacted with compounds such as chlorosulfonic acid (ClSO$_3$H) to produce the sulfonic acid derivative. The reaction can be depicted as follows:

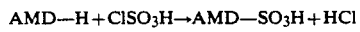

where AMD—H represents either of the two aromatic hydrogen atoms of actinomycin D.

The invention provides for actinomycin D conjugates containing all of the above actinomycin D derivatives coupled to a target cell binding protein and for methods of producing such conjugates. All of the above actinomycin D derivatives can be coupled to a target cell binding protein by a variety of means. Such coupling reactions can be achieved at a position on actinomycin D, such as the derivatized moiety, and under conditions which do not affect the function of actinomycin D, and on the antibody at a site which maintains the specificity and affinity of the antigen binding site. The actinomycin D conjugates coupled in such a way should preferably be stable to physiological conditions present during administration to a patient and transport to the target cell location. Covalent attachment of the actinomycin D derivative to the target cell binding protein is preferable for such stability.

Coupling of isocyanate and thioisocyanate derivatives of actinomycin D to a target cell binding protein can be accomplished, for example, via reaction of the isocyanate moiety with a hydroxyl or primary amine reactive group on the target cell binding protein. Of these two reactive groups, the primary amine is preferred for reaction with the isocyanate. The reaction between the isocyanate and the hydroxyl or primary amine groups tends to occur rapidly and is therefore beneficial for the efficient production of the actinomycin D conjugates.

In a similar manner, the carboxylic acid derivatives of actinomycin D can also be coupled directly to a target cell binding protein. For these actinomycin D derivatives, the carboxylic acid moiety can be, for example, activated prior to coupling with a primary amine on the protein to produce an amide bond between the actinomycin D derivative and the target cell binding protein. Coupling of the carboxylic acid derivative through other reactive groups can also be used to form an actinomycin D conjugate and are known to one skilled in the art.

In a similar manner, aldehyde and sulfonic acid derivatives of actinomycin D can be directly coupled to a target cell binding protein to produce actinomycin D conjugates. Both of these derivatives are reactive with primary amine groups of lysines, for example. Aldehydes can be coupled through a schiff base formation while sulfonic acid derivatives can be activated prior to coupling.

Formation of actinomycin D conjugates with methylene bromide derivatives of actinomycin can be accomplished using spacers. The spacer should be selected so that one end is reactive with the methylene moiety of the methylene bromide group and the other end able to be coupled to a target cell binding protein as defined above. A spacer such as 4-carboxy-sodium-phenolate (NaO—Ar—COOH), which contains an aromatic oxygen atom at one end for reaction with methylene bromide and a carboxylic acid at the other end, is one such example.

The end on the spacer containing the carboxylic acid moiety remains free after coupling to methylene bromide derivatives of actinomycin D and available for coupling to a target cell binding protein. Alternatively, the spacer can first be attached to a target cell binding protein and then coupled to a methylene bromide derivative of actinomycin D. Reactive groups other than carboxylic acid moieties can also be used on the free end of the spacer. For example, primary amines can be used to couple the free end of a spacer to a target cell binding protein and thereby form an actinomycin D conjugate.

The invention also provides for the use of spacers to produce actinomycin D conjugates with isocyanate, thioisocyanate, carboxylic acids, aldehydes and sulfonic acid derivatives of actinomycin D as well. The spacer molecule can be of a variety of types depending upon the actinomycin D derivative being coupled to the target cell binding protein. The preferred features being that the spacer contain reactive groups appropriate for the specific derivative being coupled. For example, to form a conjugate with an isocyanate or thioisocyanate derivative, the spacer should contain at one end a hydroxyl, or more preferably, a primary amine for attachment through the isocyanate or thioisocyanate moiety of the derivative. The other end can contain, for example, a carboxylic acid for coupling to a target cell binding protein.

Likewise, a spacer can be used with carboxylic acid derivatives of actinomycin D so long as one end can react with the carboxylic acid moiety, such as a primary amine and the other end is able to be coupled to a target cell binding protein. Other examples of heterobifunctional spacers for carboxylic acid derivatives of actinomycin D can include aminocarboxylic acids, mercaptocarboxylic acids, and hydroxycarboxylic acids. These spacers yield intermediates having either urea, thiourethane or urethane spacer groups, respectively. The terminal carboxylic acid moiety of such spacers can be activated to form amide bonds with lysine moieties, for example, of a target cell binding protein. Aldehydes and sulfonic acid derivatives can be similarly coupled through appropriate reactive groups on spacers. Analogous reactions to those described above for directly coupling aldehydes and sulfonic acid derivatives to a target cell binding protein can be used to couple, for example, to a spacer and then to a target cell binding protein.

The order of reaction used for coupling an actinomycin D derivative to a target cell binding protein is determined by the specific chemistries of bonding used and follow either the sequence of first attaching the linker to the actinomycin D derivative and finally attaching to the target cell binding protein, or first attaching the linker to the target cell binding protein followed by attachment to the actinomycin D derivative. The chemistry and order for the above coupling reactions is well known to one skilled in the art and is reviewed in M. J. Embleton and M. C. Garnett, Monoclonal Antibody for Cancer Detection and Therapy, Academic Press 16:317-343 (1985); Ghose et al., Methods of Enzymology, Academic Press 93:280-338 (1983); H. Tae, Bifunctional Reagents, Methods Enz. 91:580 (1983), all of which are incorporated herein by reference.

Since actinomycin D works by acting upon DNA molecules, it can be coupled to any target cell binding protein which is selective for a molecule on a DNA containing target cell. Such molecules can include, for example, viral or bacterial antigens. A derivative of actinomycin D can be prepared for coupling, for example, to any antibody or antibody fragment of the desired target specificity. Actinomycin D derivatives can also be prepared for coupling to other types of target cell binding proteins, such as hormones, growth factors and cell surface binding proteins of various types. All of these types of proteins demonstrate binding specificity toward specific target cell molecules.

The actinomycin D conjugates of the present invention can be used to produce cytotoxic effects on target cells. For example, it is possible to use actinomycin D conjugates to destroy a certain population of cells such as T cells or B cells in an organism by coupling an actinomycin D derivative to a target cell binding protein which exhibits binding specificity to the desired population of T or B cells. In a similar manner, a specific cell type can be purified from a contaminating population of cells in culture by treating the culture with an actinomycin D conjugate in which the target cell binding protein has binding specificity for the contaminating cell type. Therefore, the invention provides a method of producing cytotoxic effects on target cells by administering to the target cells an effective amount of an actinomycin D conjugate which exhibits selective binding to target cells. The conjugate can be combined with a pharmaceutically acceptable carrier.

The following examples are intended to illustrate, but not limit, the invention.

EXAMPLE I

Reaction of Actinomycin D with Oxalyl Chloride

In a 10 ml round bottom flask 10 mg actinomycin D was dissolved in 1 ml butyl acetate and 1 ml chlorobenzene was then added. The solution, which turned red, was stirred while 20 µl oxalyl chloride was added. A gas evolved vigorously and the solution turned dark red. The flask was heated for 0.1 hours, then another 20 µl of oxalyl chloride was added. The color changed from dark blood red to pale yellow. The mixture was warmed and stirred for 18 hours. A 20 µl sample was removed and placed on a NaCl disc. Solvent was evaporated and infrared spectroscopy (IR) was conducted. Sharp peaks were observed at 2360 and 2341 corresponding to NCO groups of the newly formed isocyanate derivative of actinomycin D.

The residue after vacuum distillation was a yellow solid.

The above reaction was repeated using ethyl acetate as the initial solvent for the actinomycin D and heat. The product was evaporated and redissolved in dimethyl acetate (DMAc) (10 mg/300 μl).

EXAMPLE II

Reaction of Actinomycin D - Oxalyl Chloride Derivative with Antibody

Reaction of monoclonal antibody 9.2.27, 1 ml (6 mg) was done with 100 μl of DMAc solution containing the isocyanate derivative of actinomycin D (10 mg/500 μl, 2 mg actinomycin D), prepared as indicated in Example I. The conjugate mixture was gel filtered on a PD-10 column (Pharmacia, Piscataway, N.J.), as recommended by the manufacturer.

After gel filtration, the second half of this sample, 0.5 ml, was reacted with 3 mg of carbodiimide and the pH was lowered to 6.7. The reaction was allowed to proceed for 2 hours and the material was again gel filtered on a PD-10 column.

The resulting conjugate was analyzed and the molar ratio of actinomycin D to the antibody was calculated to be 17, based on $\epsilon_{actinomycin\ D}=6.5\times10^6$, $OD_{437\ nm}$ (optical density) actinomycin D=0.371, 10:1 dilution; antibody concentration 5 mg/ml, MW (molecular weight) 155,000 g/mole.

EXAMPLE III

Methyl Group Bromination of Actinomycin D

Bromination with N-bromosuccinimide (NBS) is accomplished by adding 2.24 mmoles of actinomycin D in chlorobenzene to 2 mmoles of NBS and a trace of dibenzoyl peroxide. The mixture is heated to 80° C. and allowed to react for 6 hours. The yield of AMD—$CH_2Br$ is 70–80%. The brominated derivative is then reacted further with aminocaprioic acid to yield an AMD-aminocaproic acid complex (AMD—$CH_2NH(CH_2)_5COOH$).

EXAMPLE IV

Oxidation of Methyl Groups on Actinomycin D

Equal molar amounts of actinomycin D and ceric ammonium nitrate in 50% aqueous acetic acid is heated at 60° C. for 24 hours to produce the aldehyde derivative in 60% yield. The coupling of the aldehyde derivative to antibody is done through lysine groups by adding 20 μl 200 mM carbonate buffer to the aldehyde derivative at pH 9.5 and 8 mg of antibody. The mixture is stirred for 2 hours at room temperature. Then, 0.1 μl of sodium borohydride (4 μg/μl in water) and incubating 2 hours at 4° C.

EXAMPLE V

Sulfonic Acid Derivatives of Actinomycin D

A solution of actinomycin D in dimethylformamide (DMF) is cooled to 0° C. and an equal molar amount of chlorosulfonic acid in methylene chloride is added dropwise. The reaction mixture is warmed to room temperature and purged with nitrogen until all Hcl is removed yielding the sulfonic acid derivative.

EXAMPLE VI

Immunoreactivity of Actinomycin D conjugates

To assess whether the actinomycin D conjugates retain binding activity and antigen specificity, an ELISA is performed on target and non-target cell lines. The target cell line expresses antigens which are specifically recognized by the target cell binding protein which is coupled to actinomycin D derivatives. The non-target cell lines do not express such antigens.

Appropriate cell lines that are in logarithmic growth phase are harvested using 1 mM EDTA. The cells are centrifuged at 1000×g and rinsed 2 times with 1×PBS. The cell pellet is resuspended in 1×PBS in a volume to equal $1\times10^6$ cells/ml. Using a 12 channel micropipettor, cells are platted out in 50 μl/well volume to equal $5\times10^4$ cells/well in flexible 96 well plates. The 96 well plates are placed in a dry 37° C. incubator for 3 to 5 days until the wells are completely dry. The plates are tested with purified monoclonal antibody standards before using in specificity assays.

The above prepared dry cell plates (both target and non-target cells) are coated with 200 μl of 0.5% BSA in PBS (0.5% BAS/PBS. The plates are placed on a shaker for 1 hour at room temperature and then washed with 0.5% BSA/PBS in the following manner. For the first wash, 300 μl of 0.5% BSA/PBS is added and immediately flicked out followed by slapping dry in a teri towel. For the remaining washes, 300 μl of 0.5% BSA/PBS is added and allowed to incubate at room temperature for 3–5 minutes before flicking dry. Following the final wash, the plates are slapped dry on a teri towel.

To the above prepared and washed plates, standards and samples are added in 100 μl volumes/well starting at 10 μg/ml with serial dilutions down to 1 pg/ml. The samples are diluted in 0.5% BSA/PBS and are incubated for 1 hour at room temperature while shaking. Following incubation, the plates are washed as described above and 100 μl/well of secondary antibody (goat anti-mouse coupled to horseradish peroxide (BioRad Laboratories, Richmond, CA) is added at 1:4000 dilution in 0.5% BSA/PBS. The antibody is allowed to bind for 30 minutes while shaking at room temperature. The plates are again washed as described above and peroxidase staining is developed for 5–20 minutes with shaking by addition of 100 μl/well of OPD/Phos-citrate buffer (40 ml of phosphate-citrate buffer, 12 mg o-phenylene-diamine, 6 μl $H_2O_2$). Reactions are quenched by addition of 50 μl/well of 4N sulfuric acid and read at 490 nm on a titertek Multiskan MCC/340 elisa reader.

EXAMPLE VII

In Vitro Cytotoxicity of Actinomycin D Conjugates

Thymidine incorporation into DNA was used as a measure of viable, dividing cells after treatment with an actinomycin D conjugate.

The conjugate prepared in Example II was evaluated for in vitro cytotoxicity as follows. $10^4$M21-UCLA melanoma cells were grown in individual wells of a 96-well plate, at 37° C. with 10% $CO_2$. The cells were grown in 100 μl of RPMI 1640 (GIBCO, Grand Island, N.Y.) and 10% Fetal Bovine Serum (FBS). After 24 hours, the media was removed and replaced with 100 μl of RPMI 1640 containing concentrations ranging from $10^{-12}$ to $10^{-5}$M of the immunoconjugate. After a 24 hour incubation 1 μCi/well of $^3$H-thymidine was added to measure DNA synthesis. The cells were labeled for 24 hours and the plates were then shock frozen at −70° C., thawed at 37° C. and the cells were harvested using a PHD cell harvester (Cambridge Technology, Inc., Cambridge, Mass.) as recommended by the manufacturer. The filters from the collected samples were placed in 4 mls of Ecolune scint (ICN Biomedicals, Costa Mesa, Calif.) and placed in a Beckman liquid scintillation counter (Beckman, Carlsbad, Calif.). The results of this in vitro assay indicated a high level of cytotoxicity for the antibody-actinomycin D conjugate.

EXAMPLE VIII

Iodination of the Conjugate

The immunoconjugates prepared as described in Example II were iodinated using IodoGen from Pierce (Pierce, Rockford, Ill.). 2 mg of IodoGen was dissolved in 4.7 ml of chloroform and between 120-240 μl of this solution was aliquoted into polystyrene tubes for iodination. The tubes were placed on ice and between 50-500 μg of actinomycin D conjugate in 100 μl was added. Na$^{125}$I was added to 0.5-1.0 μCi and mixed. The mixture was incubated on ice for 25 minutes with gentle shaking. Unreacted $^{125}$I was removed from the labeled actinomycin D conjugate by gel filtration in PBS using a PD10 column (Pharmacia, Pleasant Hill, Calif.).

EXAMPLE IX

In Vivo Binding of Conjugate

The antibody-actinomycin D conjugate from Example II was evaluated for in vivo binding specificity and affinity.

Figure 2:
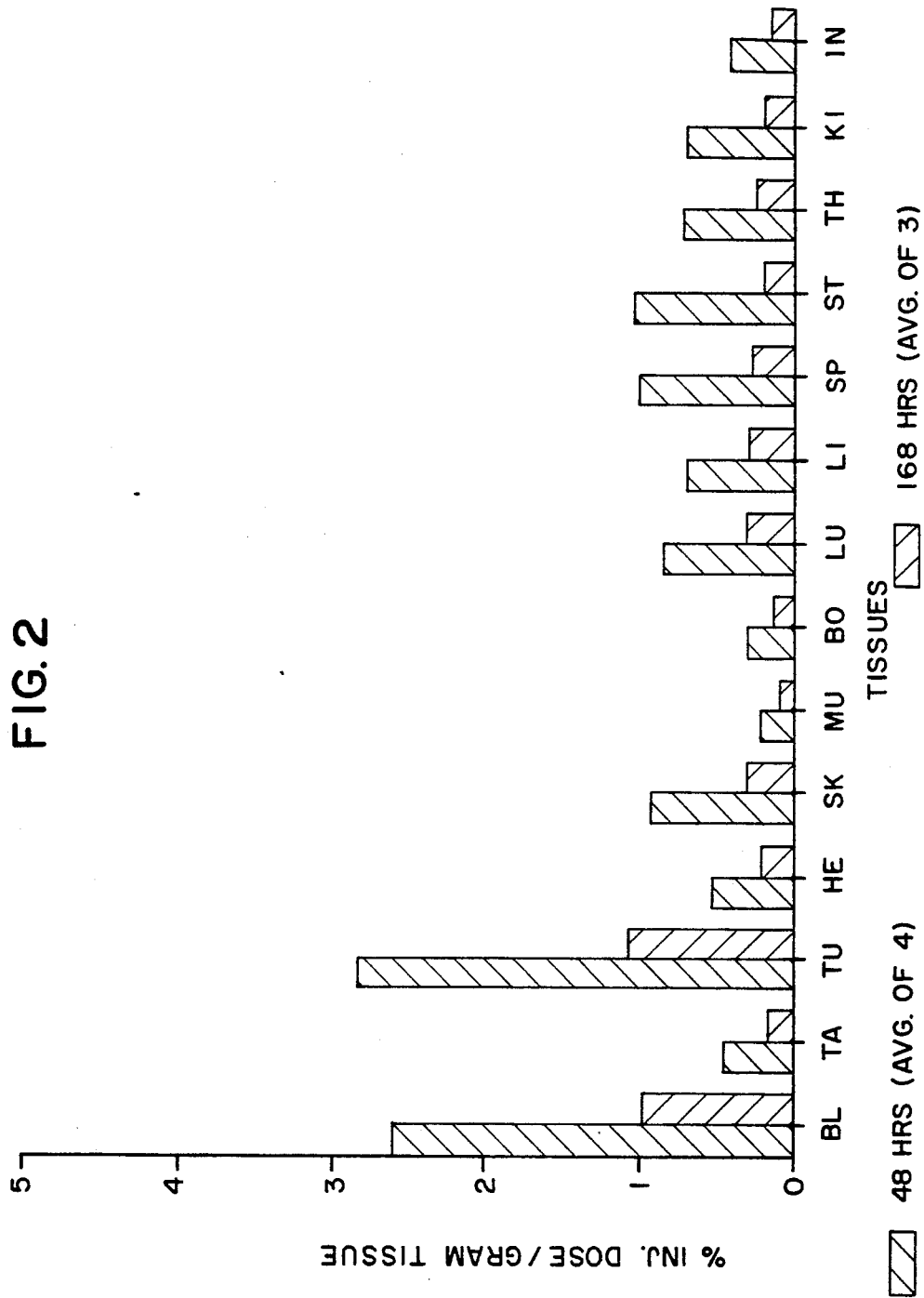
FIG. 2 shows the in vivo binding and distribution of a $^{125}I$ labeled actinomycin D conjugate. The indicated tissues are: BL, blood; TA, tail; TU, tumor; HE, heart; SK, skin; MU, muscle; BO, bone; LU, lung; LI, liver; SP, spleen; ST, stomach; TH, thyroid; KI, kidney; IN, intestine.

Thymus deficient BALBc (nude/nude) mice were subcutaneously injected with $2 \times 10^6$M21-UCLA melanoma cells. After two weeks, 3 μCi of $^{125}$I immunoconjugate prepared as described in Example VIII, was injected into the tail vein. At 48 and 168 hours the animals were sacrificed and the radioactivity in individual organs was determined by Scintillation counting. The results are shown in FIG. 2 and are represented as the percent of injected radioactivity per gram of tissue. The 48 hour samples were determined from the average of four animals. The 168 hour samples were determined from the average of three animals. The tissues indicated are: BL, blood; TA, tail; TU, tumor; HE, heart; SK, skin; MU, muscle; BO, bones; LU, lung; LI, liver; SP, spleen; ST, stomach; TH, thyroid; KI, kidney; IN, intestine.

The in vivo biodistribution data obtained with tumor bearing nude mice showed that the conjugate had a high degree of binding specificity and affinity. Further, the data indicated that any unbound conjugate was cleared from the body as shown by the relatively lower levels of conjugate found in the liver, kidney, spleen and intestine.

Although the invention has been described with reference to the presently preferred embodiment, it should be understood that various modifications can be made without departing from the spirit of the invention. Accordingly, the invention is limited only by the claims.

I claim:

1. A conjugate comprising an actinomycin D derivative of the formula

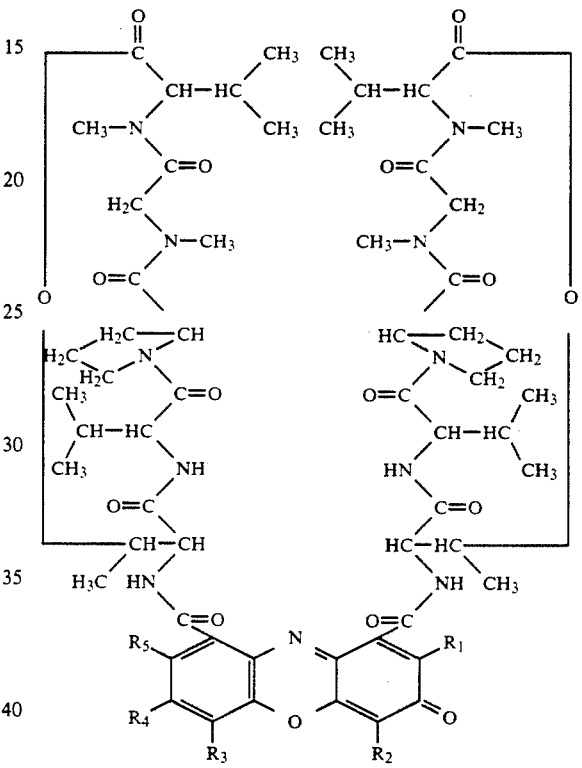

wherein $R_1$ is NCO, $NH_2$, $NHCH_2CO_2H$, or NHCORX where R is a hydrocarbon and X is selected from the group consisting of NCO, $CO_2H$, NCS;

$R_2$ and $R_3$ are $CH_3$, $CH_2Br$ or CHO;

$R_4$ and $R_5$ are H or $SO_3H$ with the proviso that the combination of groups at $R_1$, $R_2$, $R_3$, $R_4$ and $R_5$ does not yield actinomycin D as shown in FIG. 1a.

2. The conjugate of claim 1, wherein said actinomycin D derivative is coupled to a target cell binding protein through the derivatized moiety.

3. The conjugate of claim 2, wherein said target cell binding protein is selected from the group consisting of an antibody, hormone, growth factor and cell surface binding protein, or functional fragment thereof.

4. The conjugate of claim 1, wherein said actinomycin D derivative is coupled to a spacer through the derivatized moiety.

5. The conjugate of claim 1, wherein said actinomycin D derivative is coupled through a spacer to a target call binding protein, said coupling is through the derivatized moiety on actinomycin D.

6. The conjugate of claim 5, wherein said target cell binding protein is selected from the group consisting of an antibody, hormone, growth factor and cell surface binding protein, or functional fragment thereof.

* * * * *